US009364475B2

(12) United States Patent
Parikh et al.

(10) Patent No.: US 9,364,475 B2
(45) Date of Patent: Jun. 14, 2016

(54) TABLET FORMULATION OF A PHOSPHATIDYLINOSITOL 3-KINASE INHIBITOR

(71) Applicant: Sanofi, Paris (FR)

(72) Inventors: Darshan Parikh, Bridgewater, NJ (US); Praveen Raju, Bangalore (IN)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/645,947

(22) Filed: Mar. 12, 2015

(65) Prior Publication Data

US 2015/0246038 A1 Sep. 3, 2015

Related U.S. Application Data

(63) Continuation of application No. PCT/EP2013/036066, filed on Sep. 13, 2013.

(60) Provisional application No. 61/743,980, filed on Sep. 14, 2012.

(30) Foreign Application Priority Data

Jul. 22, 2013 (FR) ...................................... 13 57180

(51) Int. Cl.

| A61K 31/498 | (2006.01) |
| A61K 9/28 | (2006.01) |
| A61K 9/20 | (2006.01) |
| A61K 31/337 | (2006.01) |
| A61K 45/06 | (2006.01) |
| A61K 31/517 | (2006.01) |
| A61K 31/555 | (2006.01) |

(52) U.S. Cl.
CPC ............ *A61K 31/498* (2013.01); *A61K 9/2009* (2013.01); *A61K 9/2054* (2013.01); *A61K 9/2059* (2013.01); *A61K 9/286* (2013.01); *A61K 9/2813* (2013.01); *A61K 9/2866* (2013.01); *A61K 31/337* (2013.01); *A61K 31/517* (2013.01); *A61K 31/555* (2013.01); *A61K 45/06* (2013.01)

(58) Field of Classification Search
None
See application file for complete search history.

(56) References Cited

FOREIGN PATENT DOCUMENTS

WO WO 2012/065057 5/2012
WO WO2014/041144 A1 * 3/2014 ........... C07D 241/44

OTHER PUBLICATIONS

International Search Report for WO2014/041142 dated Mar. 20, 2014.

Berge, et al., Pharmaceutical Salts, Journal of Phmaraceutical Sciences, (1977), vol. 66, No. 1, pp. 1-19.
Sridhar, et al., Protein Kinases as Therapeutic Targets, Pharmaceutical Research, vol. 17, No. 11, (2000), pp. 1345-1353.
Park, et al., A Novel Mechanism of TRAF Signaling Revealed by Structural and Functional Analyses of the TRADD-TRAF2 Interaction, Cell, vol. 101, pp. 777-787. (2000).
Campbell, et al., Mutation of the PIK3CA Gene in Ovarian and Breast Cancer, Cancer Research, vol. 64, pp. 7678-7681, (2004).
Levine, et al., Frequent Mutation of the PIK3CA Gene in Ovarian, Clin Cancer Res. (2005), vol. 11, No. 8, (2005), pp. 2875-2876.
Wang, et al., PIK3CA Mutations in Advanced Ovanan Carcinomas, Human Mutation, (2005), vol. 25, pp. 1-5.
Lee, et al., Activation of PI3K/Akt Pathway by PTEN Reduction and PIK3CAS MRNA Amplification Contributes to Cisplatin Resistance in an Ovarian Cancer Cell Line, Gynecologic Oncology, vol. 97, (2005), pp. 26-34.
Li, et al., PIK3CA Mutations in Breast Cancer are Associated With Poor Outcome, Breast Cancer Research and Treatment, (2006), vol. 96, pp. 91-95.
Saal, et al., PIK3CA Mutations Correlate With Hormone Receptors, Node Metastasis, and ERBB2, and Are Mutually Exclusive With PTEN Loss in Human Breast Carcinoma, Cancer Research, (2005), vol. 65. No. 7, pp. 2554-2559.
Samuels, et al., High Frequency of Mutations of the PIK3CA Gene in Human Cancers, Science, (2004), vol. 304, p. 554.
Velho, et al., The Prevalence of PIK3CA Mutations in Gastric and Colon Cancer, European Journal of Cancer, vol. 41, (2005), pp. 1649-1654.
Oda, et al., High Frequency of Coexistent Mutants of PIK3CA and PTEN Genes in Endometrial Carcinoma, Cancer Research, (2005), vol. 65, No. 23, pp. 10669-10673.
Byun, et al., Frequent Monoallelic Deletion of PTEN and Its Reciprocal Association With PIK3CA Amplification in Gastric Carcinoma, Int. J. Cancer, vol. 104, pp. 318-327, (2003).
Lee, et al., PIK3CA Gene is Frequently Mutated in Breast Carcinomas and Hepatocellular Carcinomas, Oncogene, (2005), vol. 24, pp. 1477-1480.
Tang, et al., Phosphorylated Akt Overexpression and Loss of PTEN Expression in Non-Small Cell Lung Cancer Confers Poor Prognosis, Lung Cancer, (2006). vol. 51, pp. 181-191.
Wu, et al., Uncommon Mutation, But Common Amplifications, of the PIK3CA Gene in Thyroid Tumors, The Journal of Clinical Endocrinology & Metabolism, vol. 90, No. 8, pp. 4688-4693.
Sujobert, et al., Essential Role for the p110δ Isoform in Phosphoinositide 3-Kinase Activation and Cell Proliferation in Acute Myeloid Leukemia, Blood, vol. 106, No. 3, pp. 1063-1066, (2005).
Hartmann, et al., PIK3CA Mutations in Glioblestoma Multiforme, Acta Neuropathol, (2005), vol. 109, pp. 639-642.
Bachman, et al., The PIK3CA Gene is Mutated With High Frequency in Human Breast Cancers, Cancer Biology & Therapy, vol. 3, No. 9, pp. 772-775, (2004).
Samuels, et al., Oncogenic Mutations or PIK3CA in Human Cancers, Cell Cycle, vol. 3, No. 10, pp. e17-e19, (2004).

(Continued)

*Primary Examiner* — Brian J Davis
(74) *Attorney, Agent, or Firm* — Brian R. Morrill

(57) ABSTRACT

The present invention is directed to compositions and methods that target the PI3K signaling pathway for the treatment or prevention of cancer. In one aspect, there is provided a pharmaceutical formulation comprising Polymorph E of N-(3-{[(2Z)-3-[(2-chloro-5-methoxyphenyl)amino]quinoxalin-2(1H)-ylidene]sulfamoyl}phenyl)-2-methylalaninamide.

32 Claims, 5 Drawing Sheets

(56) References Cited

OTHER PUBLICATIONS

Massion, et al., Early Involvement of the Phosphatidylinositol 3-Kinase/Akt Pathway in Lung Cancer Progression, American Journal of Respiratory and Critical Care Medicine, vol. 170, pp. 1068-1094 (2004).

Hickey, et al., BCR-ABL Regulates Phosphatidylinositol 3-Kinase-P110 Transcription and Activation and is Required for Proliferation and Drug Resistance, Journal of Biological Chemistry, vol. 281, No. 5. pp. 2441-2450, (2006).

* cited by examiner

TABLET FORMULATION OF A PHOSPHATIDYLINOSITOL 3-KINASE INHIBITOR

BACKGROUND

According to National Cancer Institute statistics, 41% of men and women alive today will be diagnosed with cancer at some point in their lives. The widespread occurrence of this disease underscores the need for improved anticancer regimens for the treatment of malignancy.

One important drug target is a group of proteins called kinases. Protein kinases are a large and diverse family of enzymes that catalyze protein phosphorylation and play a critical role in cellular signaling. They may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with proto-oncogenes and tumor suppressor genes have been well documented. Similarly, the connection between diabetes and related conditions, and deregulated levels of protein kinases, has been demonstrated. See e.g., Sridhar et al. Pharmaceutical Research, 17(11): 1345-1353 (2000). Viral infections and the conditions related thereto also have been associated with the regulation of protein kinases. Park et al. Cell 101 (7), 777-787 (2000).

Phosphatidylinositol 3-kinase (PI3K or PIK3CA) is composed of an 85 kDa regulatory subunit and a 110 kDa catalytic subunit. The protein encoded by this gene represents the catalytic subunit, which uses ATP to phosphorylate PtdIns, PtdIns4P and PtdIns(4,5)P2. PTEN, a tumor suppressor which inhibits cell growth through multiple mechanisms, can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

PI3Kα has been implicated in the control of cytoskeletal reorganization, apoptosis, vesicular trafficking, proliferation and differentiation processes. Increased copy number and expression of PIK3CA is associated with a number of malignancies such as ovarian cancer (Campbell et al., Cancer Res 2004, 64, 7678-7681; Levine et al., Clin Cancer Res 2005, 11, 2875-2878; Wang et al., Hum Mutat 2005, 25, 322; Lee et al., Gynecol Oncol 2005, 97, 26-34), cervical cancer, breast cancer (Bachman, et al. Cancer Biol Ther 2004, 3, 772-775; Li et al., Breast Cancer Res Treat 2006, 96, 91-95; Saal et al., Cancer Res 2005, 65, 2554-2559; Samuels and Velculescu, Cell Cycle 2004, 3, 1221-1224), colorectal cancer (Samuels, et al. Science 2004, 304, 554; Velho et al. Eur J Cancer 2005, 41, 1649-1654), endometrial cancer (Oda et al. Cancer Res. 2005, 65, 10669-10673), gastric carcinomas (Byun et al., Int J Cancer 2003, 104, 318-327; Lee et al., Oncogene 2005, 24, 1477-1480), hepatocellular carcinoma (Lee et al., Oncogene 2005, 24, 1477-1480), small and non-small cell lung cancer (Tang et al., Lung Cancer 2006, 51, 181-191; Massion et al., Am J Respir Crit Care Med 2004, 170, 1088-1094), thyroid carcinoma (Wu et al., J Clin Endocrinol Metab 2005, 90, 4688-4693), acute myelogenous leukemia (AML) (Sujobert et al., Blood 1997, 106, 1063-1066), chronic myelogenous leukemia (CML) (Hickey and Cotter J Biol Chem 2006, 281, 2441-2450), and glioblastomas (Hartmann et al. Acta Neuropathol (Berl) 2005, 109, 639-642).

A number of PI3K inhibitors are presently undergoing clinical evaluation in patients with cancer, the details of which can be reviewed at the web site ClinicalTrials.gov. For example, human clinical trials are underway to evaluate a form of N-(3-{[(2Z)-3-[(2-chloro-5-methoxyphenyl)amino] quinoxalin-2(1H)-ylidene]sulfamoyl}phenyl)-2-methylalaninamide in patients with lymphoma (See trial NCT00486135), non-small-cell lung cancer (See trial NCT00692640), endometrial cancer (See trials NCT01013324 and NCT00756847) breast cancer (See trials NCT01042925 and NCT01082068) or other solid tumor (See trials NCT01357330, NCT01390818 and NCT01436565). In light the compound's established biological activity, optimized forms are needed to achieve maximal patient efficacy.

SUMMARY

Accordingly, there is an ongoing need for new compositions and methods that specifically target the PI3K signaling pathway for the treatment or prevention of cancer.

In one aspect, provided herein is a pharmaceutical formulation comprising Polymorph E of N-(3-{[(2Z)-3-[(2-chloro-5-methoxyphenyl)amino]quinoxalin-2(1H)-ylidene] sulfamoyl}phenyl)-2-methylalaninamide, a hydrogel polymer, and a diluent. In one embodiment, the hydrogel is selected from the group consisting of microcrystalline cellulose, methyl cellulose, hydroxymethyl cellulose, polyvinyl pyrrolidone, hydroxyethyl cellulose, hydroxypropyl cellulose, hydroxypropyl methylcellulose, polyethylene oxides, gums, acrylate polymers and methacrylate polymers. In another embodiment, the hydrogel is microcrystalline cellulose. In an embodiment, the diluent can be selected from the group consisting of sugars, starches or vegetable oils, lactose monohydrate, calcium phosphate, dextrin, dextrose, maltitol, maltose, starch, sucrose or talc. In one embodiment, the diluent is a starch, such as pregelatinized starch or sodium starch glycolate.

In another aspect, provided herein is a pharmaceutical formulation comprising 40-60%, by weight, of Polymorph E of N-(3-{[(2Z)-3-[(2-chloro-5-methoxyphenyl)amino]quinoxalin-2(1H)-ylidene]sulfamoyl}phenyl)-2-methylalaninamide; 15-35%, by weight, of microcrystalline cellulose; 5-15%, by weight, of pregelatinized starch; and between 0.1-10.0%, by weight, each, of hypromellose, silicon dioxide, and sodium starch glycolate.

In one embodiment, the pharmaceutical formulations provided above are in tablet form. In another embodiment, the pharmaceutical formulations provided above are in an immediate-release tablet form. The formulations can comprise approximately 50 mg, 100 mg, 150 mg, or 200 mg of Polymorph E.

In another aspect, compressed solid dosage forms are provided comprising Polymorph E of N-(3-{[(2Z)-3-[(2-chloro-5-methoxyphenyl)amino]quinoxalin-2(1H)-ylidene] sulfamoyl}phenyl)-2-methylalaninamide, a hydrogel polymer and a diluent. The dosage form can comprise, by weight, 40-60% Polymorph E; 15-35% microcrystalline cellulose; 5-15% pregelatinized starch and between 0.1-10.0% each of hypromellose, silicon dioxide and sodium starch glycolate. In another example, the dosage form can comprise, by weight, about 50% Polymorph E; about 27% microcrystalline cellulose; about 10% pregelatinized starch, about 3% hypromellose, about 1% silicon dioxide and about 4% sodium starch glycolate. The dosage form can comprise about 40 to 250 mg of Polymorph E or about 50 mg, 100 mg, 150 mg or 200 mg of Polymorph E. In one embodiment, the dosage form is a tablet, while in another it is a caplet.

In another aspect, a compressed solid dosage form is provided comprising A) an active agent containing an effective amount of Polymorph E of N-(3-{[(2Z)-3-[(2-chloro-5-methoxyphenyl)amino]quinoxalin-2(1H)-ylidene]sulfamoyl}phenyl)-2-methylalaninamide, and B) at least one pharmaceutically acceptable additive, wherein the active agent is present in an amount of more than about 40% by weight based upon the total weight of the compressed solid dosage form. The dosage form can comprise, by weight, 40-60% Polymorph E; 15-35% microcrystalline cellulose; 5-15% pregelatinized starch and between 0.1-10.0% each of hypromellose, silicon dioxide and sodium starch glycolate. In another example, the dosage form can comprise, by weight, about 50% Polymorph E; about 27% microcrystalline cellulose; about 10% pregelatinized starch, about 3% hypromellose, about 1% silicon dioxide and about 4% sodium starch glycolate.

In one embodiment, the active agent of the dosage form comprises at least 95% Polymorph E. In another, the active agent of the dosage form comprises at least 97% Polymorph E, while in another it comprises at least 99% Polymorph E.

In another aspect, provided herein is a method of treating cancer in a subject, comprising administering to the subject in need thereof the above pharmaceutical formulations. In an embodiment, the cancer is a solid tumor or lymphoma. In an embodiment, the lymphoma is a relapsed or refractory lymphoma. In an embodiment, the lymphoma is lymphocytic lymphoma (CLL) or small lymphocytic lymphoma (SLL).

In one embodiment, the cancer is breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), or thyroid carcinoma. In another embodiment, the cancer is metastatic or unresectable. The treatment also can comprise the administration of an additional anticancer agent. Non-limiting examples of such agents include carboplatin, paclitaxel, erlotinib, or trastuzumab.

In another embodiment, kits are provided comprising pharmaceutical formulations comprising polymorph E of the compound N-(3-{[(2Z)-3-[(2-chloro-5-methoxyphenyl)amino]quinoxalin-2(1H)-ylidene]sulfamoyl}phenyl)-2-methylalaninamide. In one example, the kit contains a pharmaceutical composition comprising polymorph E of N-(3-{[(2Z)-3-[(2-chloro-5-methoxyphenyl)amino]quinoxalin-2(1H)-ylidene]sulfamoyl}phenyl)-2-methylalaninamide. In one embodiment, the kit comprises instructions for using the compound or pharmaceutical composition to treat a patient with cancer.

Other objects, features and advantages will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

DETAILED DESCRIPTION

Figure 1:
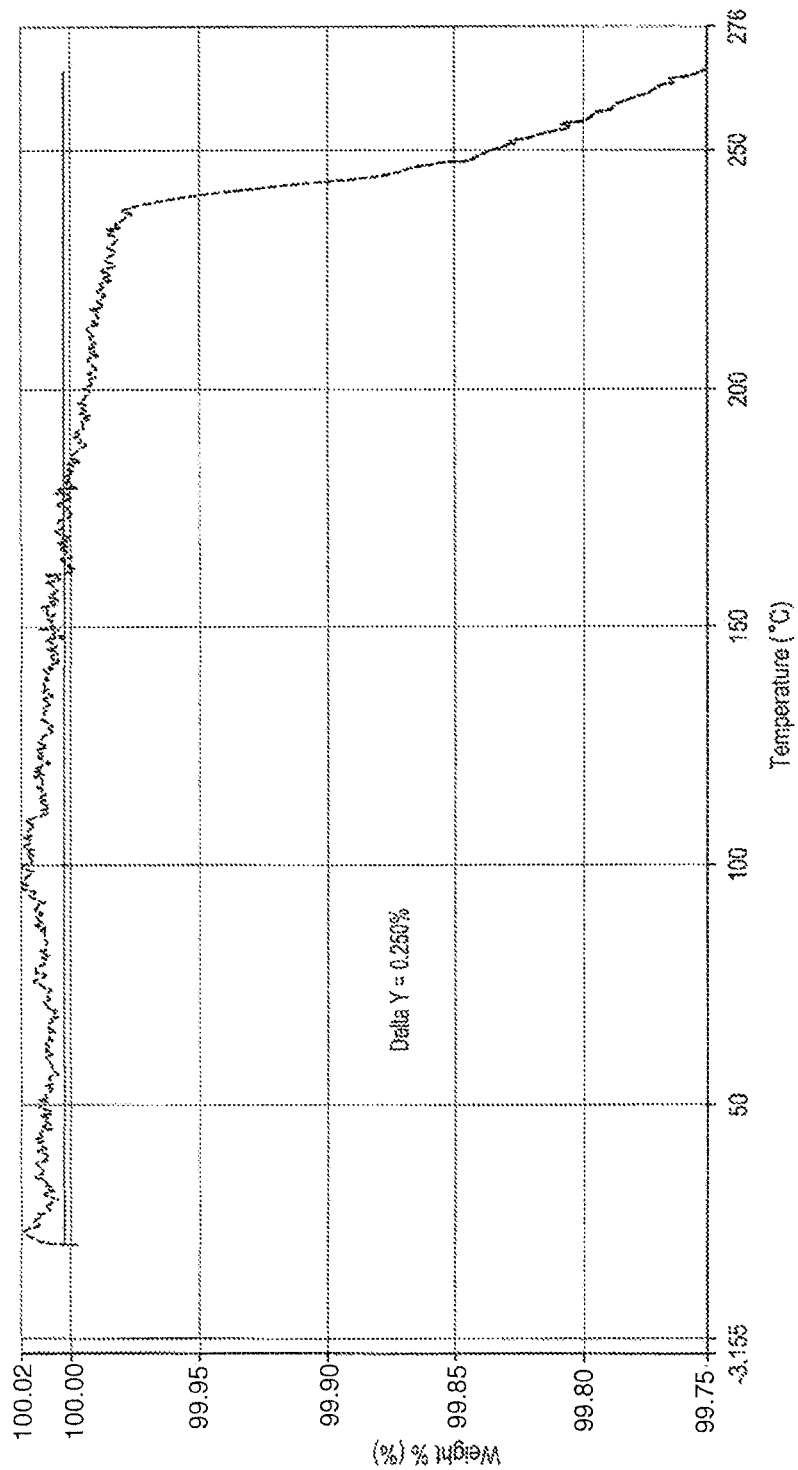
FIG. 1 depicts results of a thermogravimetric analysis of polymorph E.

Pharmaceutical formulations are provided comprising Polymorph E of N-(3-{[(2Z)-3-[(2-chloro-5-methoxyphenyl)amino]quinoxalin-2(1H)-ylidene]sulfamoyl}phenyl)-2-methylalaninamide, a hydrogel polymer, and a diluent. Compressed solid dosage forms comprising Polymorph E also are provided. The inventive compositions, which are useful for treating cancer, possess superior features over prior forms of N-(3-{[(2Z)-3-[(2-chloro-5-methoxyphenyl)amino]quinoxalin-2(1H)-ylidene]sulfamoyl}phenyl)-2-methylalaninamide, including greater stability.

Certain terms used herein are described below. Compounds of the present invention are described using standard nomenclature. Unless defined otherwise, all technical and scientific terms used herein have the same meaning as is commonly understood by one of skill in the art to which this invention belongs.

"N-(3-{[(2Z)-3-[(2-chloro-5-methoxyphenyl)amino]quinoxalin-2(1H)-ylidene]sulfamoyl}phenyl)-2-methylalaninamide" has the following structure:

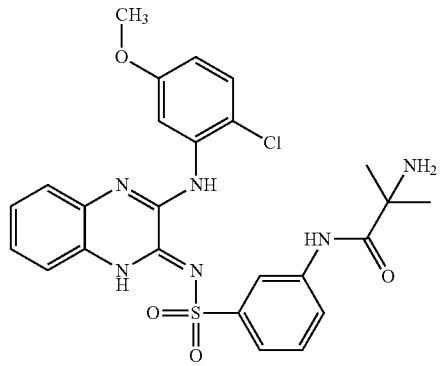 [SMILES: COc1ccc(Cl)c(Nc2nc3ccccc3[nH]/c2=N\S(=O)(=O)c2cccc(NC(=O)C(C)(C)N)c2)c1]

Throughout the application, N-(3-{[(2Z)-3-[(2-chloro-5-methoxyphenyl)amino]quinoxalin-2(1H)-ylidene]sulfamoyl}phenyl)-2-methylalaninamide, or a pharmaceutically acceptable salt or solvate thereof, is referred to as "Compound (I)." It will be recognized that N-(3-{[(2Z)-3-[(2-chloro-5-methoxyphenyl)amino]quinoxalin-2(1H)-ylidene]sulfamoyl}phenyl)-2-methylalaninamide may exist in alternate tautomeric forms. One example is N-(3-{[(3-{[2-chloro-5-(methoxy)phenyl]amino}quinoxalin-2-yl)amino]sulfonyl}phenyl)-2-methylalaninamide,

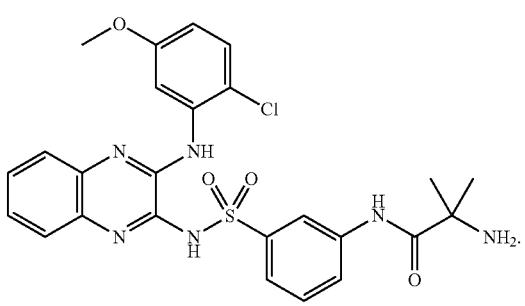 [SMILES: COc1ccc(Cl)c(Nc2nc3ccccc3nc2NS(=O)(=O)c2cccc(NC(=O)C(C)(C)N)c2)c1]

In another example, the compound may exist, for instance in solution, as a zwitterion, such as

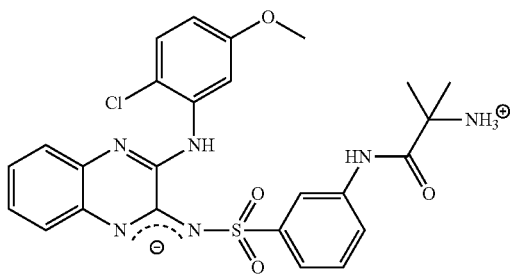 [SMILES: COc1ccc(Cl)c(NC2=Nc3ccccc3NC2NS(=O)(=O)c2cccc(NC(=O)C(C)(C)[NH3+])c2)c1]

The compound N-(3-{[(2Z)-3-[(2-chloro-5-methoxyphenyl)amino]quinoxalin-2(1H)-ylidene]sulfamoyl}phenyl)-2-methylalaninamide is a potent and selective inhibitor of PI3K (phosphatidylinositol 3-kinase) and inhibits phosphorylation of multiple downstream components of the PI3K signaling pathway in cell lines in vitro and in human xenograft tumor tissue in vivo. This activity is associated with inhibition of tumor cell proliferation and induction of apoptosis, which results in tumor growth inhibition and tumor regression in multiple human xenograft tumor models.

"Yield" for each of the reactions described herein is expressed as a percentage of the theoretical yield.

"Subject" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

The terms "effective amount" or "pharmaceutically effective amount" or "therapeutically effective amount" refer to a sufficient amount of an agent to provide the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent, and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. The amount can vary depending on such factors as the size and weight of the subject, the type of illness, or the particular compound of the invention. The amount also can vary depending on the compound, the disease state and its severity, the age of the patient to be treated, and the like. The effective amount can be determined by one of ordinary skill in the art having regard to their knowledge and to this disclosure.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

Unless otherwise indicated, "treating" or "treatment" of a disease, disorder, or syndrome, as used herein, means inhibiting the disease, disorder, or syndrome, that is, arresting its development; and relieving the disease, disorder, or syndrome, that is, causing regression of the disease, disorder, or syndrome. As is known in the art, in the context of treatment, adjustments for systemic versus localized delivery, age, body weight, general health, sex, diet, time of administration, drug interaction and the severity of the condition may be necessary, and will be ascertainable with routine experimentation by one of ordinary skill in the art.

"Prevention" means preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

As used herein, the term "about" generally indicates a possible variation of no more than 10%, 5%, or 1% of a value. For example, "about 25 mg/kg" will generally indicate, in its broadest sense, a value of 22.5-27.5 mg/kg, i.e., 25±10 mg/kg.

The term "oral dosage form," as used herein, means any pharmaceutical composition intended to be administered to the lower gastrointestinal tract of a human or other mammal via the mouth of said human or other mammal. For the purposes of the present invention, the delivered form can be in the form of a compressed tablet containing granules or particles of a bisphosphonate and a chelating agent, a capsule (e.g., soft gelatin or hard gelatin, consisting of starch, or hydroxypropylmethylcellulose) which contains beads, particles, or suspensions of the bisphosphonate and the chelating agent, or a dry mix containing granules or particles of bisphosphonate and chelating agent for making a reconstituted suspension in water (e.g., a sachet).

As used herein, the term "therapeutic effect" denotes achieving a desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancer, the effect may be to cause a tumor to shrink and/or to decrease the growth rate of the tumor (such as to suppress tumor growth) or to prevent or delay other unwanted cell proliferation. In some embodiments, the effect may be to delay development. In some embodiments, the effect may be to prevent or delay recurrence. In other aspects, the effect may: (i) reduce the number of cancer cells; (ii) reduce tumor size; (iii) inhibit, retard, slow to some extent, and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Polymorph E

As used herein, the term "Polymorph E" refers to the crystalline form of Compound (I) described in Example 2, herein. Polymorph E is identifiable on the basis of, for example, characteristic peaks in an X-ray powder diffraction analysis. X-ray powder diffraction, also referred to as XRPD, is a scientific technique using X-ray, neutron, or electron diffraction on powder, microcrystalline, or other solid materials for structural characterization of the materials. In one embodiment, polymorph E exhibits an X-ray powder diffraction pattern having characteristic peaks expressed in degrees 2-Theta at angles of 18.3°±0.3° and 24.4°±0.3°. In another embodiment, polymorph E exhibits characteristic peaks at angles of 18.8°±0.3° and 23.7°±0.3°. In another embodiment, polymorph E exhibits characteristic peaks at angles of 9.8°±0.3° and 23.2°±0.3°. In another embodiment, polymorph E exhibits characteristic peaks at angles of 10.1°±0.3° and 28.3°±0.3°. In another embodiment, polymorph E exhibits characteristic peaks at angles of 9.8°±0.3°, 10.1°±0.3°, 18.3°±0.3°, 18.8°±0.3°, 23.2°±0.3°, 23.7°±0.3°, 28.3°±0.3° and 24.4°±0.3°.

In other embodiments, polymorph E is identifiable on the basis of characteristic peaks in an FT-IR spectrum. FT-IR, also referred to as Fourier transform infrared spectroscopy, is a technique which is used to obtain an infrared spectrum of absorption, emission, photoconductivity or Raman scattering of a material. In one embodiment, polymorph E exhibits an FT-IR spectrum having characteristic peaks expressed in units of $cm^{-1}$ at values of about 1682, about 1296 and about 1136. In another embodiment, polymorph E exhibits an FT-IR spectrum that possesses two or more characteristic peaks (±4 $cm^{-1}$) listed in Table 1.

TABLE 1

| Wavenumber ($cm^{-1}$) |
|---|
| 3383.3 |
| 3300.3 |
| 3221.1 |
| 2957.8 |
| 2930.1 |
| 1682.0 |
| 1619.9 |
| 1593.1 |
| 1555.6 |
| 1486.9 |
| 1461.9 |
| 1404.6 |
| 1350.9 |
| 1296.2 |
| 1246.4 |
| 1216.0 |
| 1136.4 |
| 1097.7 |
| 1080.0 |
| 1023.5 |
| 973.3 |
| 935.4 |
| 912.3 |
| 860.5 |
| 842.1 |
| 790.5 |
| 767.3 |
| 744.3 |
| 714.5 |
| 685.3 |
| 666.3 |

In other embodiments, polymorph E is identifiable on the basis of a characteristic peak observed in a differential scanning calorimetry thermogram. Differential scanning calorimetry, or DSC, is a thermoanalytical technique in which the difference in the amount of heat required to increase the temperature of a sample and reference is measured as a function of temperature. In one embodiment, polymorph E exhibits a differential scanning calorimetry thermogram having a characteristic peak expressed in units of ° C. at a temperature of about 232±2° C. (e.g., 232.6±2° C.).

In another embodiment, polymorph E exhibits a melting point expressed in units of ° C. at a temperature in the range of about 230-235. In one embodiment, polymorph E exhibits a melting point expressed in units of ° C. at a temperature in the rage of about 231-233. In certain embodiments, polymorph E has an enthalpy of fusion of about 114 J/g.

In some embodiments, polymorph E is identifiable on the basis of a characteristic thermogravimetry curve. Thermogravimetry, also referred to as TG, involves analysis (i.e., thermogravimetric analysis) based on a continuous recording of mass changes of a sample of material as a function of a combination of temperature, time, and in some instances pressure. In one embodiment, polymorph E exhibits a thermogravimetry curve substantially in accordance with FIG. 1.

Polymorph E proved to be the most stable polymorphic form of N-(3-{[(2Z)-3-[(2-chloro-5-methoxyphenyl)amino]quinoxalin-2(1H)-ylidene]sulfamoyl}phenyl)-2-methylalaninamide evaluated. In light of its superior performance characteristics, polymorph E was selected as the crystal form of N-(3-{[(2Z)-3-[(2-chloro-5-methoxyphenyl)amino]quinoxalin-2(1H)-ylidene]sulfamoyl}phenyl)-2-methylalaninamide for use in pharmaceutical compositions.

Pharmaceutical Formulations Comprising Polymorph E

With the elucidation and selection of a new polymorphic form of Compound (I), a new pharmaceutical formulation was developed. Factorial studies were performed and optimal substituents and concentration levels were discovered. For example, it was determined that a range of 5-15% of pregelatinized starch could be used to yield enhanced early dissolution rates of a tablet, with 10% providing the best performance. In another example, 3% was determined to be the optimal quantity of hypromellose, which yields enhanced tablet compressability and dissolution profile. In another example, it was discovered that the use of 1% colloidal silicon dioxide in external phase produced better flowability of granules.

Thus, in one aspect, a pharmaceutical formulation is provided comprising Polymorph E of N-(3-{[(2Z)-3-[(2-chloro-5-methoxyphenyl)amino]quinoxalin-2(1H)-ylidene]sulfamoyl}phenyl)-2-methylalaninamide, a hydrogel polymer, and a diluent. In one embodiment, the hydrogel is selected from the group consisting of microcrystalline cellulose, methyl cellulose, hydroxymethyl cellulose, polyvinyl pyrrolidone, hydroxyethyl cellulose, hydroxypropyl cellulose, hydroxypropyl methylcellulose, polyethylene oxides, gums, acrylate polymers and methacrylate polymers. In another embodiment, the hydrogel is microcrystalline cellulose. In one embodiment, the diluent can be selected from the group consisting of sugars, starches or vegetable oils, lactose monohydrate, calcium phosphate, dextrin, dextrose, maltitol, maltose, starch, sucrose or talc. In one embodiment, the diluent is a starch, such as pregelatinized starch or sodium starch glycolate.

In one embodiment, a pharmaceutical formulation is provided comprising 40-60%, by weight, of Polymorph E of N-(3-{[(2Z)-3-[(2-chloro-5-methoxyphenyl)amino]quinoxalin-2(1H)-ylidene]sulfamoyl}phenyl)-2-methylalaninamide; 15-35%, by weight, of microcrystalline cellulose; 5-15%, by weight, of pregelatinized starch; and between 0.1-10.0%, by weight, each, of hypromellose, silicon dioxide, and sodium starch glycolate.

In another aspect, the pharmaceutical formulation comprises, by weight, 40-60% Polymorph E; 15-35% microcrystalline cellulose; 5-15% pregelatinized starch and between 0.1-10.0% each of hypromellose, silicon dioxide and sodium starch glycolate. In another embodiment, the pharmaceutical formulation comprises, by weight, about 50% Polymorph E; about 27% microcrystalline cellulose; about 10% pregelatinized starch, about 3% hypromellose, about 1% silicon dioxide and about 4% sodium starch glycolate.

In another embodiment, the pharmaceutical formulations provided above are in tablet form. In another embodiment, the pharmaceutical formulations provided above are in an immediate-release tablet form. The formulations can comprise approximately 50 mg, 100 mg, 150 mg, or 200 mg of Polymorph E.

In another aspect, compressed solid dosage forms are provided for ease of ingestion. In particular, compressed solid dosage forms are provided comprising Polymorph E of N-(3-{[(2Z)-3-[(2-chloro-5-methoxyphenyl)amino]quinoxalin-2(1H)-ylidene]sulfamoyl}phenyl)-2-methylalaninamide, a hydrogel polymer and a diluent. The dosage form can comprise, by weight, 40-60% Polymorph E; 15-35% microcrystalline cellulose; 5-15% pregelatinized starch and between 0.1-10.0% each of hypromellose, silicon dioxide and sodium starch glycolate. In another example, the dosage form can comprise, by weight, about 50% Polymorph E; about 27% microcrystalline cellulose; about 10% pregelatinized starch, about 3% hypromellose, about 1% silicon dioxide and about 4% sodium starch glycolate. The dosage form can comprise about 40 to 250 mg of Polymorph E or about 50 mg, 100 mg, 150 mg or 200 mg of Polymorph E. In one embodiment, the dosage form is a tablet, while in another it is a caplet.

In another aspect, a compressed solid dosage form is provided comprising A) an active agent containing an effective amount of Polymorph E of N-(3-{[(2Z)-3-[(2-chloro-5-methoxyphenyl)amino]quinoxalin-2(1H)-ylidene]sulfamoyl}phenyl)-2-methylalaninamide, and B) at least one pharmaceutically acceptable additive, wherein the active agent is present in an amount of more than about 40% by weight based upon the total weight of the compressed solid dosage form. The dosage form can comprise, by weight, 40-60% Polymorph E; 15-35% microcrystalline cellulose; 5-15% pregelatinized starch and between 0.1-10.0% each of hypromellose, silicon dioxide and sodium starch glycolate. In another example, the dosage form can comprise, by weight, about 50% Polymorph E; about 27% microcrystalline cellulose; about 10% pregelatinized starch, about 3% hypromellose, about 1% silicon dioxide and about 4% sodium starch glycolate.

In one embodiment, the active agent of the dosage form comprises at least 95% Polymorph E. In another, the active agent of the dosage form comprises at least 97% Polymorph E, while in another it comprises at least 99% Polymorph E.

In another embodiment, the pharmaceutical formulations provided above are in an immediate-release tablet form. "Immediate release" refers to a dosage form which releases the active ingredient substantially immediately upon contact with gastric juices and will result in substantially complete dissolution within about 1 hour.

The formulations can comprise about 50 mg, 100 mg, 150 mg, or 200 mg of Polymorph E.

In some embodiments, pharmaceutical compositions comprising Polymorph E may take the form of film-coated tablets as detailed in Table 2.

TABLE 2

Composition of Polymorph E 50 mg film-coated tablets

| Components | Composition per unit [mg/unit] | | Function | Reference to standards[a] |
|---|---|---|---|---|
| | 50 mg | 200 mg | | |
| Core tablet | | | | |
| Internal phase | | | | |
| Polymorph E | 50.0 | 200.0 | Drug substance | |
| Microcrystalline cellulose 90 μm | 27.0 | 108.0 | Diluent | Ph. Eur.-NF |
| Pregelatinized starch | 10.0 | 40.0 | Diluent | Ph. Eur.-NF |
| Hypromellose 6 mPa·s | 3.0 | 12.0 | Binder | Ph. Eur.-USP |
| Colloidal anhydrous silica-Colloidal silicon dioxide | 1.0 | 4.0 | Flow aid | Ph. Eur.-NF |
| Sodium starch glycolate (type A) | 4.0 | 16.0 | Disintegrant | Ph. Eur.-NF |
| Purified water[b] | — | — | Granulation agent | Ph. Eur.-USP |
| External phase | | | | |
| Sodium starch glycolate (type A) | 3.0 | 12.0 | Disintegrant | Ph. Eur.-NF |
| Colloidal anhydrous silica-Colloidal silicon dioxide | 1.0 | 4.0 | Flow aid | Ph. Eur.-NF |
| Magnesium stearate vegetable 6-12 m²/g | 1.0 | 4.0 | Lubricant | Ph. Eur.-NF |
| Core tablet terminated at | 100.0 | 400.0 | | |
| Film-coating | | | | |
| Opadry® II 33G94107 pink[c] | 5.0 | 20.0 | Film-coating agent | |
| Purified water[b] | — | — | Film-coating solvent | Ph. Eur.-USP |
| Film-coated tablet terminated at | 105.0 mg | 420.0 mg | | |

[a] When a Pharmacopeia is referred to, then the current edition of this Pharmacopoeia is applied.
[b] Removed during manufacture.
[c] Composed of lactose monohydrate Ph. Eur.-NF-JP (21%), hypromellose 6 mPa·s Ph. Eur.-USP-JP (40%), titanium dioxide Ph. Eur.-USP-JP (24.830%), macrogol-PEG 3350 Ph. Eur.-NF (8%), triacetin Ph. Eur.-USP-JPE (6%) and iron oxide red NF-JPE (0.170%).

Preparation of Pharmaceutical Formulation Comprising Polymorph E

Figure 2:
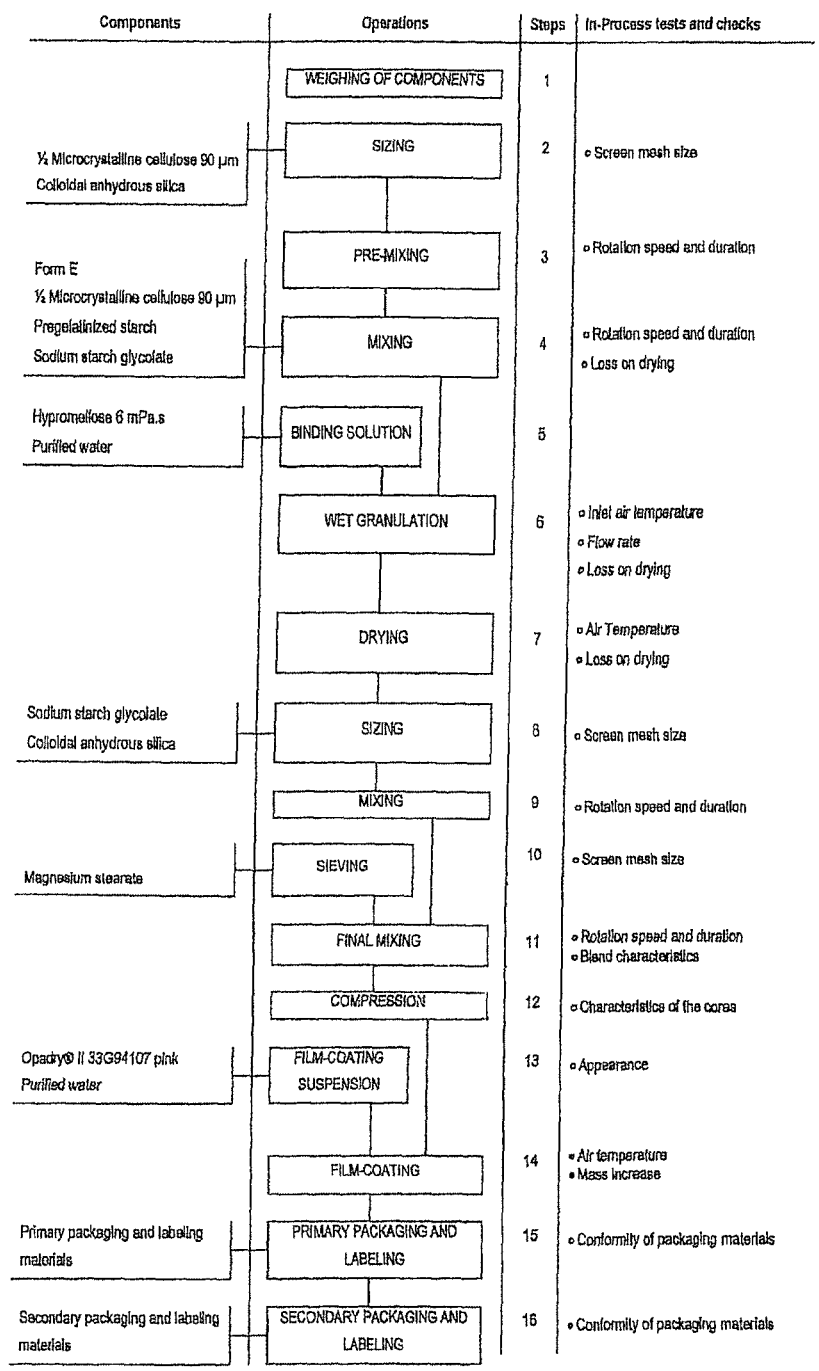
FIG. 2 depicts a flow diagram of a manufacturing process for a pharmaceutical formulation comprising Polymorph E

The flow diagram provided in FIG. 2 depicts a manufacturing process, including in-process controls, for preparing Polymorph E film-coated tablets. In line with the diagram, Polymorph E film-coated tablets can be prepared via the following steps:

1. Weigh all the components.
2. Sieve half of microcrystalline cellulose and colloidal anhydrous silica for internal phase through a 1 mm screen mesh size.
3. Mix components sieved at step 2 for about 2 minutes at about 7 r/min.
4. Add Polymorph E, remaining microcrystalline cellulose, pregelatinized starch and sodium starch glycolate for internal phase then proceed to the mixing for about 10 minutes at about 7 r/min.
5. Prepare the binding solution by adding hypromellose 6 mPa·s under stirring conditions into purified water and mix for about 30 minutes. Let degazing before use.
6. Charge the blend into a fluid bed granulator previously heated. Add the binding solution to the blend with an inlet air temperature of 65±5° C. and proceed to granulation.
7. Dry the wet granules using an inlet air temperature of 65±5° C. until a loss on drying similar to that obtained on the dry blend is achieved.
8. Pass the dried granules, colloidal anhydrous silica and sodium starch glycolate for external phase on a 1 mm screen mesh size.
9. Mix for about 15 minutes at about 7 r/min
10. Sieve magnesium stearate through a 0.8 mm screen mesh size.
11. Add magnesium stearate previously sieved to the mix and proceed to final mixing for about 15 minutes at about 7 r/min to obtain a homogeneous blend.
12. Compress the lubricated granules on a rotative press fitted with either 9×4 mm punches at a nominal mass of 100 mg per 50 mg tablet or with 6.35×14.30 mm punches at a nominal mass of 400 mg per 200 mg tablet.
13. Prepare in a mixing tank a sufficient amount of the film-coating suspension by mixing Opadry® II 33G94107 pink with purified water.
14. Place the tablets obtained in step 12 in a coating pan and spray the film-coating suspension onto the cores with an inlet air temperature of 62±5° C. Continue the coating process until not less than 5 mg of coating material is applied for 50 mg tablets and not less than 20 mg of coating material for 200 mg tablets.
15. Perform the primary packaging and labeling operations.
16. Perform the secondary packaging and labeling operations.

To assure identity, quality, strength, and purity of the Drug Product before use in the clinical study, the Drug Product will be tested against the specifications listed in Table 3. These specifications will be applied to tablets manufactured under current Good Manufacturing Practice (cGMP) regulations for use in the clinical studies.

TABLE 3

Specifications for Polymorph E pink film-coated tablets

| Test Name | Test Method | Acceptance Criteria | Stability |
|---|---|---|---|
| Appearance | Visual | Light pink to pink caplet film-coated tablet | X |
| Identification test | HPLC | The retention time of sample corresponds to retention time of reference (±5%) | |
| Identification test | UV | Complies to reference spectrum | |
| Assay | HPLC | 50 mg tablets: 45.0-55.0 mg/unit of Polymorph E<br>200 mg tablets: 180.0-220.0 mg/unit of Polymorph E<br>(90.0 to 110.0% of label claim) | X |
| Degradation products | HPLC | | X |
| Rr 1.09 | | ≤0.25% | |
| SAR334884A | | ≤0.75% | |
| Any unspecified degradation product (each) | | ≤0.20% | |
| Total degradation products | | ≤4.0% | |
| Dissolution | | Q = 70 in 60 minutes | X |
| Stage I | | | |
| Number of units out of 6 < Q + 5% of label claim | USP <711><br>Ph Eur 2.9.3 | 0<br>≥Q% | |
| Stage II | | | |
| Average of 12 units | | 0 | |
| Number of units out of 12 < Q – 15% of label claim | | ≥Q% | |
| Stage III | | | |
| Average of 24 units | | ≤2 | |
| Number of units out of 24 < Q – 15% of label claim | | 0 | |
| Number of units out of 24 < Q – 25% of label claim | | | |
| Uniformity of Dosage Units by Weight variation | | | |
| Stage I | | | |
| Acceptance value for 10 units (L1) | USP <905><br>Ph Eur 2.9.40 | ≤15.0 | |
| Stage II | | | |
| Acceptance value for 30 units (L1) | | ≤15.0 | |
| Number of units outside of 0.75*M to 1.25*M | | 0 | |
| Water content | Microcoulometry | To be determined | X |
| Microbial tests | | | X* |
| Total viable aerobic count | USP <61><br>Ph Eur 2.6.12 | ≤1000 cfu/g | |
| Yeasts and molds count | | ≤100 cfu/g | |
| *Escherichia coli* | | Absence in 1 g | |

*on an annual basis

Methods of Treating Cancer with Pharmaceutical Formulations of Polymorph E

In one aspect, the invention provides a method of treating cancer in a subject, comprising administering to the subject an effective amount a pharmaceutical formulation comprising Polymorph E of N-(3-{[(2Z)-3-[(2-chloro-5-methoxyphenyl)amino]quinoxalin-2(1H)-ylidene]sulfamoyl}phenyl)-2-methylalaninamide, a hydrogel polymer, and a diluent.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adeno carcinoma, Wilms' tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin; malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In certain embodiments, the cancer is a solid tumor. In a particular embodiment, the solid tumor is metastatic or unresectable.

In certain embodiments, the cancer is a lymphoma, e.g., chronic lymphocytic lymphoma (CLL) or small lymphocytic lymphoma (SLL). In a particular embodiment, the lymphoma is a relapsed or refractory lymphoma.

In certain embodiments of the method, the pharmaceutical formulation comprising Polymorph E is formulated into a tablet. In a particular, embodiment, the tablet is an immediate-release film-coated tablet. Tablet forms of Polymorph E can be formulated to contain any required quantity of Polymorph E. In a particular embodiment, the tablet is formulated to contain 50 mg or 200 mg of 50% w/w Polymorph E free base.

In another aspect, provided herein is the use of a pharmaceutical formulation comprising Polymorph E of N-(3-{[(2Z)-3-[(2-chloro-5-methoxyphenyl)amino]quinoxalin-2(1H)-ylidene]sulfamoyl}phenyl)-2-methylalaninamide, a hydrogel polymer, and a diluent, for the preparation of a medicament for the treatment of cancer, as described above.

Administration

Administration of pharmaceutical formulations comprising polymorph E can be carried out via any of the accepted modes of administration or agents for serving similar utilities. Administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages. In a preferred embodiment, administration is by the oral route in tablet form.

In the pharmaceutical compositions disclosed herein, Polymorph E is administered in an effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. Polymorph E can be administered to a patient at dosage levels in the range of about 0.1 to about 2,000 mg per day.

The specific dosage used for children will generally be lower due to the smaller size and weight of children, and the doses can be adjusted according to size and weight factors, as well as additional factors. For example, the dosage can depend on additional factors including the requirements of the child, the severity of the condition being treated, and the pharmacological activity of the compound being used. The determination of optimum dosages for a particular child is well known to one of ordinary skill in the art. If formulated as a fixed dose, such combination products employ the compounds of this invention within the dosage range described above and the other pharmaceutically active agent(s) within approved dosage ranges. Polymorph E alternatively may be used sequentially with known pharmaceutically acceptable agent(s) when a combination formulation is inappropriate.

Kits

In another embodiment, kits are provided comprising pharmaceutical formulations comprising polymorph E of the compound N-(3-{[(2Z)-3-[(2-chloro-5-methoxyphenyl)amino]quinoxalin-2(1H)-ylidene]sulfamoyl}phenyl)-2-methylalaninamide. In one example, the kit contains a pharmaceutical composition comprising polymorph E of N-(3-{[(2Z)-3-[(2-chloro-5-methoxyphenyl)amino]quinoxalin-2(1H)-ylidene]sulfamoyl}phenyl)-2-methylalaninamide. In one embodiment, the kit comprises instructions for using the compound or pharmaceutical composition to treat a patient with cancer.

EXAMPLES

Example 1

Synthesis of Compound (I)

Figure 3:
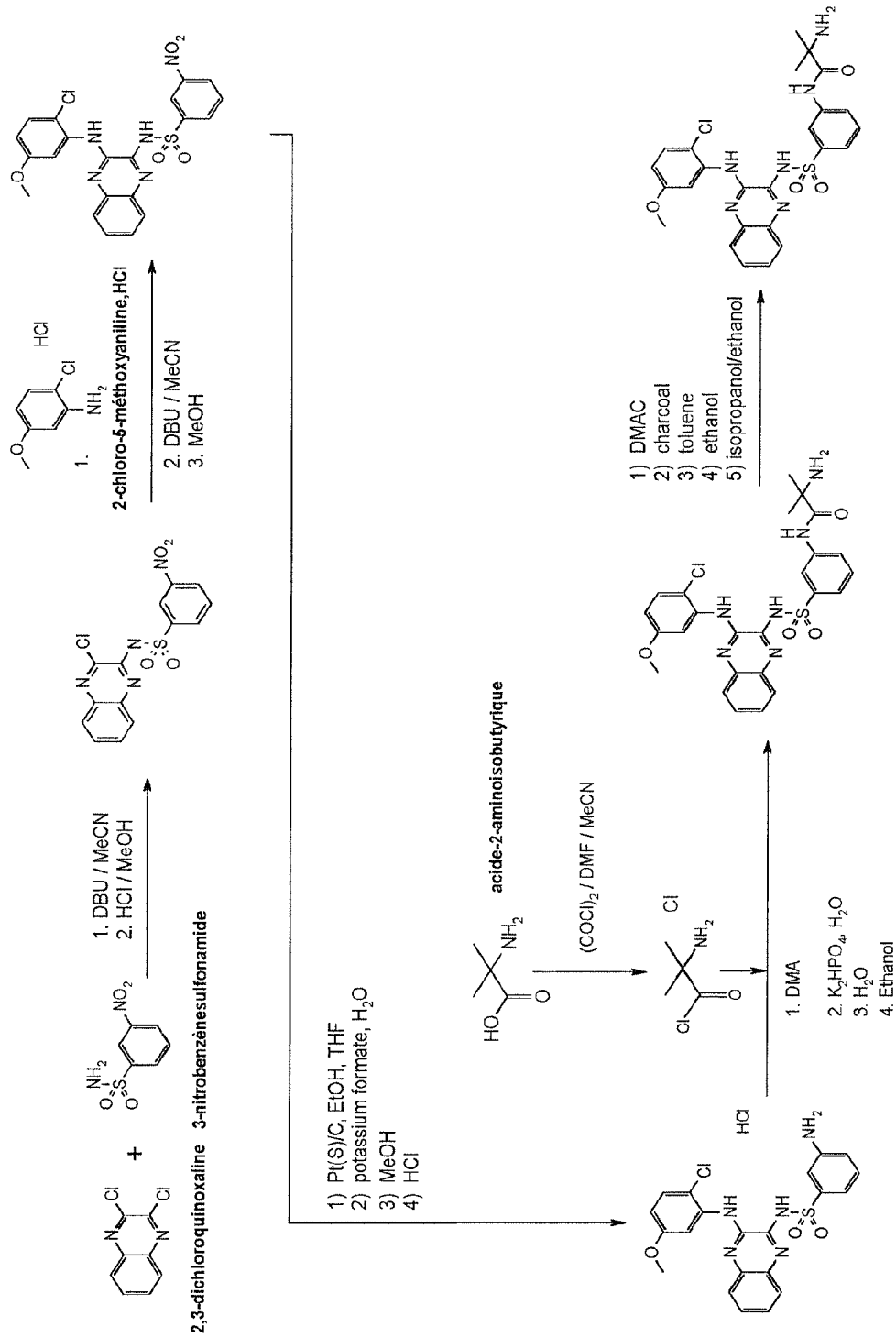
FIG. 3 depicts a synthesis scheme for preparing raw Compound (I).

FIG. 3 depicts a synthesis scheme for preparing compound (I). A description of the scheme is provided below.

Synthesis of (N-(3-chloroquinoxalin-2-yl)-3-nitrobenzenesulfonamide)

1 kg of 2,3 dichloroquinoxaline and 1 kg of 3-nitrobenzenesulfonamide are mixed in 5 volumes of acetonitrile. The reaction mixture is heated to reflux. 2.3 kg of DBU and 1 volume of acetonitrile are added. After completion of the reaction, cool down at 5° C. Add 12 volumes of methanol and 1.53 kg of HCl, filter the reaction mixture. Wash the cake with 6 volumes of methanol and dry under vacuum.

Synthesis of (N-(3-((2-chloro-5-methoxyphenyl)amino)quinoxalin-2-yl)-3-nitrobenzenesulfonamide)

Prepare a solution with 0.585 kg of 2-chloro-5-methoxyaniline-HCl, 3.5 volumes of acetonitrile and 0.46 kg of DBU. (solution A) Mix 1 kg of N-(3-chloroquinoxalin-2-yl)-3-nitrobenzenesulfonamide and 5.5 volumes of acetonitrile. Heat to reflux. Add solution A and 1 volume of acetonitrile onto the reaction mixture. After completion of the reaction at reflux, cool down at 20° C., dilute with 10 volumes of methanol and filter. Wash the cake 3 times with 5 volumes of methanol and dry it under vacuum.

Synthesis of 3-amino-N-{3-[(2-chloro-5-methoxyphenyl)amino]quinoxalin-2-yl}benzenesulfonamide hydrochloride To 1 kg of N-{3-[(2-chloro-5-methoxyphenyl)amino]quinoxalin-2-yl}-3-nitrobenzenesulfonamide, add a catalytic amount of platinum sulfide on carbon (Pt(S)C), 6 volumes of THF, 0.16 volume of water and 2 volumes of ethanol. The reaction mixture is stirred and heated to reflux. An aqueous potassium formate solution (1.4 volume of water+0.69 kg of potassium formate) is added. The reaction mixture is stirred at reflux until completion of the reaction and cooled down at 50° C. After the addition of 10 volumes of methanol and a one hour stirring, the catalyst is filtered off and washed with 3.4 volumes of methanol. The filtered solution is cooled down at 20° C. 0.62 kg of HCl are added. The reaction mixture is stirred at 20° C., cooled down at 5° C. and filtered. The cake is washed with methanol (6 volumes) and dried under vacuum.

Synthesis of N-[3-({3-[(2-chloro-5-methoxyphenyl)amino]quinoxalin-2-yl}sulfamoyl)phenyl]-2-methylalaninamide (crude)

Synthesis of 2-methylalanyl chloride hydrochloride. To 0.42 kg of 2-amino-2-methylpropanoic acid, add 3.7 volumes of acetonitrile, 0.04 volume of dimethylformamide and 0.62 kg of oxalyl chloride. The reaction mixture is stirred at 20° C. until completion of the reaction and filtered. The cake is washed twice with 1 volume of acetonitrile and dried under vacuum.

To 1 kg of 3-amino-N-{3-[(2-chloro-5-methoxyphenyl)amino]quinoxalin-2-yl}benzenesulfonamide hydrochloride, add 8 volumes of dimethylformamide and 0.385 kg of 2-methylalanyl chloride hydrochloride at 5° C. After completion of the reaction, heat at 50° C. and add a solution made of K2HPO4 (1.4 kg), water (16.5 volumes) and ethanol (7.1 volumes). Cool down the reaction mixture at 10° C., stir 2 hours at 10° C. and filter. The cake is washed 3 times with 10 volumes of water and dried under vacuum.

Crude N-(3-{[(2Z)-3-[(2-chloro-5-methoxyphenyl)amino]quinoxalin-2(1H)-ylidene]sulfamoyl}phenyl)-2-methylalaninamide was recrystallized from dimethylacetamide and toluene using charcoal, followed by reslurry in ethanol, and finally washings by isopropanol/ethanol mixture, resulting in the compound in pure form.

Surprisingly and unexpectedly, the solid state compound recovered from this process was entirely N-(3-{[(2Z)-3-[(2-chloro-5-methoxyphenyl)amino]quinoxalin-2(1H)-ylidene]sulfamoyl}phenyl)-2-methylalaninamide. That is, while a number of tautomeric forms of the compound may exist, the instant process yielded a solid compound of only N-(3-{[(2Z)-3-[(2-chloro-5-methoxyphenyl)amino]quinoxalin-2(1H)-ylidene]sulfamoyl}phenyl)-2-methylalaninamide and not a mixture of tautomers, as confirmed by ssNMR.

Example 2

Preparation of Polymorph E

The following crystallization takes place in a double jacket reactor; the temperature in the reactor is checked and controlled via the temperature in the double jacket. The stirring apparatus is a glasslock type and the speed of stirring is fixed at 350 rpm.

Figure 4:
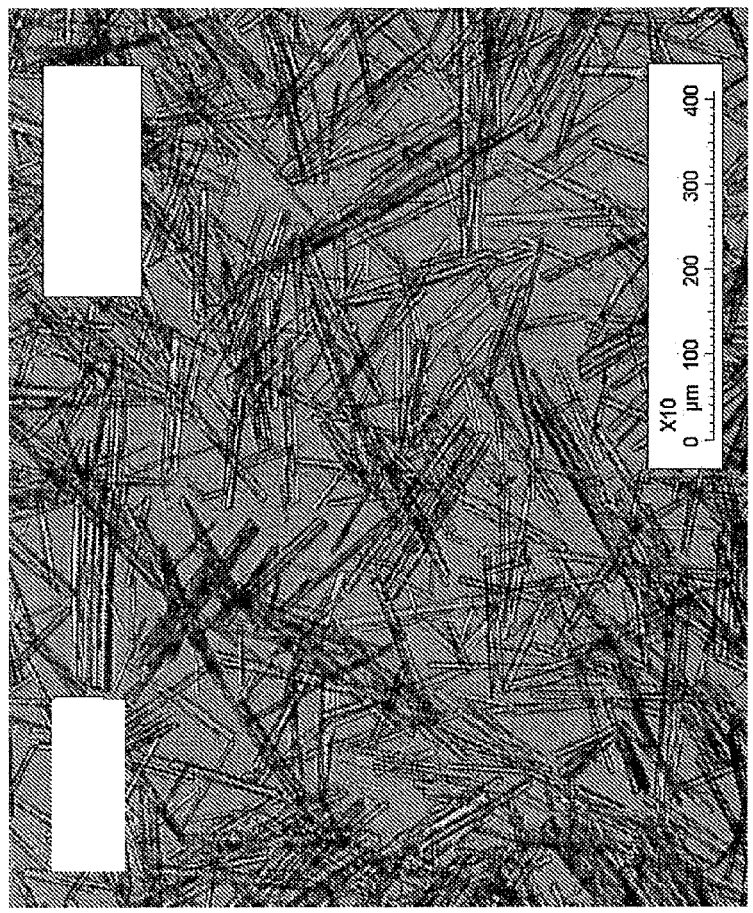
FIG. 4 depicts the results of optical microscopy of polymorph E.

10 g of raw compound (I) was combined with 10V (100 mL) of dimethylacetamide, the temperature of the double jacket is fixed at 95° C., and the compound is allowed to dissolve. The mixture is lowered to 70° C. and 5V (50 ml) of toluene is added. The crystallization begins during this time. The mixture is then heated up to 90° C., maintained one hour at that temperature and lowered to 20° C. with a cooling rate of −10° C./hour. Before filtration, an aliquot of suspension is withdrawn and observed by optical microscopy. The crystals of solvate appear under the shape of fine rods. See FIG. 4. The suspension is filtered, then washed three times: twice with isopropanol (20 ml for each of the washes), then once with ethanol (10 ml), to yield the DMAC solvate of compound (I).

Figure 5:
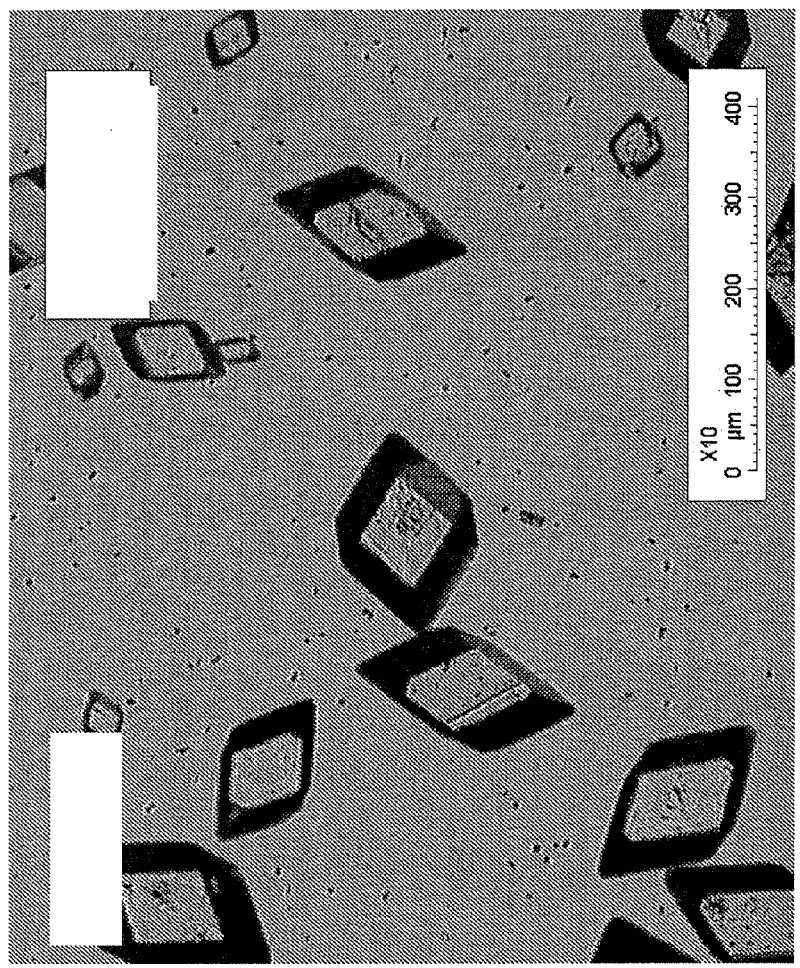
FIG. 5 depicts additional results of optical microscopy of polymorph E.

The wet powder is re-slurried in 10 Volumes of ethanol at the temperature of 50° C., with a speed of stirring of 200 rpm, and then seeded with 1% (w/w) of polymorph E. The mixture is maintained in isotherm under stirring for several hours. The polymorphic conversion to polymorph E takes place during this stage. The temperature is lowered again to 50° C. for filtration. This transformation can be followed by optical microscopy, by Raman spectroscopy and Lasentec probe. The crystals of polymorph E appear in the shape of rhombohedric particles. See FIG. 5.

When the transformation is complete, the mixture is filtered at 50° C., then crystals are washed once with isopropanol (20 ml) and again with a volume of ethanol (10 ml). Crystals are dried in statics (vacuum tray dryer or oven ventilated tray dryer at the respective temperatures of 70° C. and 110° C.) for 12 at least hours.

What is claimed is:

1. A pharmaceutical formulation comprising Polymorph E of N-(3-{[(2Z)-3-[(2-chloro-5-methoxyphenyl)amino]quinoxalin-2(1H)-ylidene]sulfamoyl}phenyl)-2-methylalaninamide, a hydrogel polymer and a diluent.

2. The pharmaceutical formulation of claim 1, wherein the hydrogel is selected from the group consisting of microcrystalline cellulose, methyl cellulose, hydroxymethyl cellulose, polyvinyl pyrrolidone, hydroxyethyl cellulose, hydroxypropyl cellulose, hydroxypropyl methylcellulose, polyethylene oxides, gums, acrylate polymers and methacrylate polymers.

3. The pharmaceutical formulation of claim 1, wherein the hydrogel is microcrystalline cellulose.

4. The pharmaceutical formulation of claim 1, wherein the diluent is selected from the group consisting of sugars, starches, vegetable oils, lactose monohydrate, calcium phosphate, dextrin, dextrose, maltitol, maltose, starch, sucrose and talc.

5. The pharmaceutical formulation of claim 1, wherein the diluent is a starch, and the starch is pregelatinized starch or sodium starch glycolate.

6. The pharmaceutical formulation of claim 1 comprising, by weight, 40-60% Polymorph E; 15-35% microcrystalline cellulose; 5-15% pregelatinized starch and between 0.1-10.0% each of hypromellose, silicon dioxide and sodium starch glycolate.

7. The pharmaceutical formulation of claim 1 comprising, by weight, about 50% Polymorph E; about 27% microcrystalline cellulose; about 10% pregelatinized starch, about 3% hypromellose, about 1% silicon dioxide and about 4% sodium starch glycolate.

8. The pharmaceutical formulation of claim 1, wherein the pharmaceutical formulation is in tablet form.

9. The pharmaceutical formulation of claim 8, wherein the pharmaceutical formulation is in caplet form.

10. The pharmaceutical formulation of claim 8, wherein the pharmaceutical formulation is an immediate-release tablet form.

11. The pharmaceutical formulation of claim 1, wherein the formulation comprises about 50 mg, 100 mg, 150 mg, or 200 mg of Polymorph E.

12. A compressed solid dosage form comprising Polymorph E of N-(3-{[(2Z)-3-[(2-chloro-5-methoxyphenyl)amino]quinoxalin-2(1H)-ylidene]sulfamoyl}phenyl)-2-methylalaninamide, a hydrogel polymer and a diluent.

13. The dosage form of claim 12, comprising, by weight, 40-60% Polymorph E; 15-35% microcrystalline cellulose; 5-15% pregelatinized starch and between 0.1-10.0% each of hypromellose, silicon dioxide and sodium starch glycolate.

14. The dosage form of claim 13 comprising, by weight, about 50% Polymorph E; about 27% microcrystalline cellulose; about 10% pregelatinized starch, about 3% hypromellose, about 1% silicon dioxide and about 4% sodium starch glycolate.

15. The dosage form of claim 12, wherein the dosage form comprises about 40 to 250 mg of Polymorph E.

16. The dosage form of claim 12, wherein the dosage form comprises about 50 mg, 100 mg, 150 mg or 200 mg of Polymorph E.

17. The dosage form of claim 12, wherein the dosage form is a tablet.

18. The dosage form of claim 17, wherein the dosage form is a caplet.

19. A compressed solid dosage form comprising:
A) an active agent containing Polymorph E of N-(3-{[(2Z)-3-[(2-chloro-5-methoxyphenyl)amino]quinoxalin-2(1H)-ylidene]sulfamoyl}phenyl)-2-methylalaninamide, and
B) at least one pharmaceutically acceptable additive,
wherein the active agent is present in an amount of more than about 40% by weight based upon the total weight of the compressed solid dosage form.

20. The dosage form of claim 19, comprising, by weight, 40-60% Polymorph E; 15-35% microcrystalline cellulose; 5-15% pregelatinized starch and between 0.1-10.0% each of hypromellose, silicon dioxide and sodium starch glycolate.

21. The dosage form of claim 20 comprising, by weight, about 50% Polymorph E; about 27% microcrystalline cellulose; about 10% pregelatinized starch, about 3% hypromellose, about 1% silicon dioxide and about 4% sodium starch glycolate.

22. The dosage form of claim 19, wherein the active agent comprises at least 95% Polymorph E.

23. The dosage form of claim 22, wherein the active agent comprises at least 97% Polymorph E.

24. The dosage form of claim 23, wherein the active agent comprises at least 99% Polymorph E.

25. A method of treating cancer in a subject, comprising administering to the subject the pharmaceutical formulation of claim 1.

26. A method of treating cancer in a subject, comprising administering to the subject the dosage form of claim 1.

27. The method of claim 25, wherein the cancer is a solid tumor or lymphoma.

28. The method of claim 27, wherein the lymphoma is a relapsed or refractory lymphoma.

29. The method of claim 27, wherein the lymphoma is chronic lymphocytic lymphoma (CLL) or small lymphocytic lymphoma (SLL).

30. The method of claim 25, wherein the cancer is breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), or thyroid carcinoma.

31. The method of claim 25, wherein the treatment comprises the administration of an additional anticancer agent.

32. The method of claim 31, wherein the anticancer agent is carboplatin, paclitaxel, erlotinib, or trastuzumab.

* * * * *